May 4, 1965 D. SEWART Plant Pat. 2,502
CHAMOMILE PLANT
Filed Feb. 26, 1964
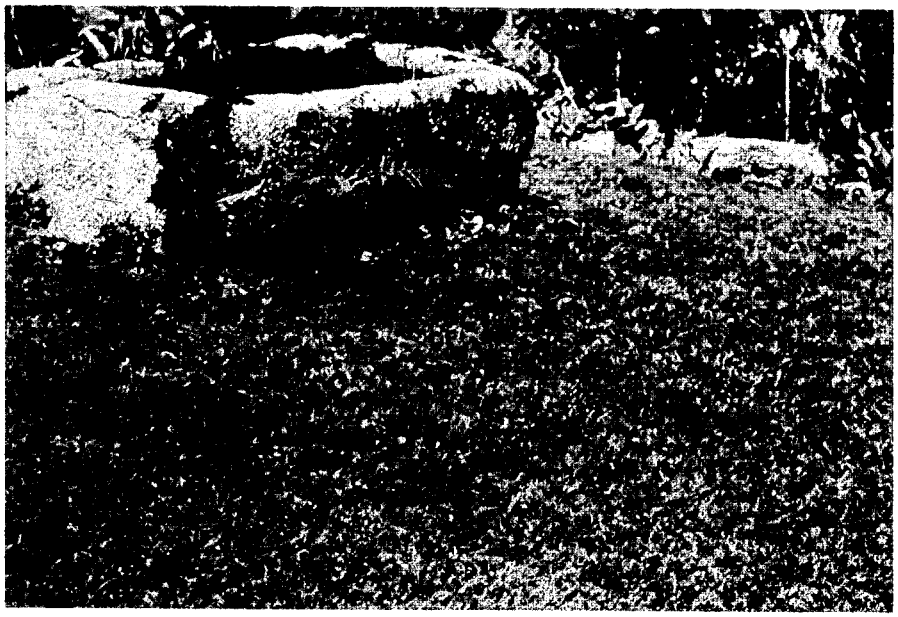
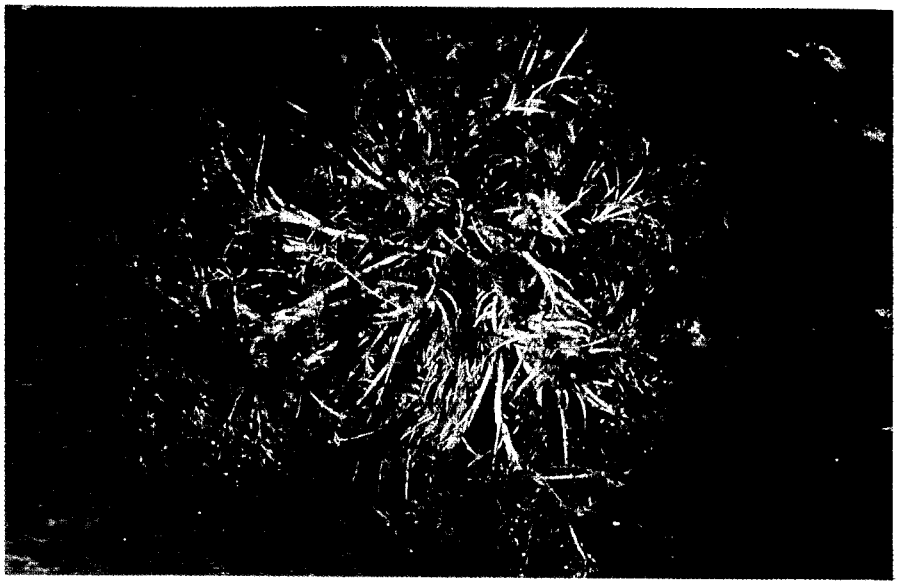
Inventor
Dorothy Sewart
by Robb & Robb
attorneys United States Patent Office Plant Pat. 2,502
Patented May 4, 1965

2,502
CHAMOMILE PLANT

Dorothy Sewart, Lower Treneague, Wadebridge, Cornwall, England

Filed Feb. 26, 1964, Ser. No. 347,636
1 Claim. (Cl. Plt.—88)

My present invention comprises a new and distinct variety of chamomile plant which is a sport of the ordinary variety known as *Anthemis nobilis.*

The object of this invention has been to provide a new chamomile which is absolutely flowerless and as such reduces to practically nothing the amount of care required where the said chamomile is used as a lawn or sward.

The variety *Anthemis nobilis* is as old as lawn making virtually, and has always heretofore produced a number of flowers on long straggling stalks, although there is a double variety which is known to have somewhat fewer flowers.

The plant of my present invention has many of the same characteristics as the parent variety but it is difficult to distinguish the same from the parent variety because of the many similarities and it is primarily distinguishable by reason of its lack of flowers.

The variety is non-flowering perennial as stated, and a pleasantly scented herb which in ancient times was used by herbalists for medicinal and other purposes. However the lack of flowers of the instant variety obviates the use for this purpose and on the other hand has made the same very desirable for lawns since it keeps green in the hottest summer and grows right up to the boles of trees.

Where chamomile lawns have heretofore been planted, the ever present necessity for mowing the same has been present in order to keep the flower stems down.

Another feature of the instant variety is the fact that it spreads sideways rapidly by stem rootings and in a relatively short time a large number of rooted plants form which may be potted separately.

An important advantage of the instant variety is the fact that it will grow in shady areas where grass has been difficult if not impossible to grow and the pleasantly scented aspect of the plant with short, much branched creeping root stock and spreading decumbent stems forms a very pleasant lawn.

Growth is very vigorous, the plant spreading by means of short runners as before stated, which are produced freely around the parent plant. As an example, one rooted off-set may, in one year, form a plant covering an area nine inches in diameter, making a soft, thick sward one and one-half to two inches deep.

The much disected leaves on cultivated specimens may be up to 2½ inches long and 2 to 3 times pinnate, the ultimate segments being short, linear-subulate and sparsely hairy.

The foliage is moss-like and after rain a pleasant fragrance arises therefrom.

The lawn is found to be hard-wearing although at the same time soft and springy, maintaining its good green color substantially throughout the year.

Another important advantage of this new variety of chamomile is its ability to smother weeds and provide covering for banks which are cut to shape for various decorative purposes.

This variety of chamomile has been grown continuously in the area known as Treneague, in Cornwall, England, where it has been planted in lawns and similar areas, plants of my new variety growing vigorously as stated.

My new variety has been asexually reproduced by cuttings in the vicinity of Treneague, Wadebridge, Cornwall, England.

My new variety has been found to retain its distinctive characteristics through successive asexual reproduction.

The accompanying drawing forming a part thereof shows a typical plant of my new variety of chamomile in color as nearly representative of the actual color as is possible to obtain in photographic processes. In addition to the single plant disclosed in the drawing, there is also shown a lawn or sward comprised entirely of the instant variety.

It is essential that the plants be kept separate from flowering chamomiles in order to maintain the distinctive advantage thereof, namely the virtual non-necessity to cut or weed the sward after it has once attained its normal growth and covering of the ground area desired.

There follows herein a detailed description of certain phases of my new variety of chamomile plant, the color references being to the Nickerson Color Fan published by the Munsell Color Company:

Parentage: Sport of *Anthemis nobilis* (chamomile).
Classification: *Anthemis nobilis* variety.
Flower: None.
Plant:
- *Form.*—Low, spreading perennial.
- *Growth.*—Very vigorous, sprawly, compact.
- *Height.*—Average 1½ to 2 inches.
- *Spread.*—One plant may spread to 9″ in one year.

Foliage:
- *Quantity.*—Abundant.
- *Color.*—Upper side when viewed in a mass—between 5GY 6/8 and 5GY 5/6.
- *Edge.*—Smooth.
- *Under side.*—Smooth.
- *Leaves.*—Much disected and moss-like.

I claim:

A new and distinct variety of chamomile plant substantially as herein disclosed, characterized as to novelty by the complete absence of flowers, short, much branched, creeping rootstock, spreading, decumbent stems, rapid growth by stem rootings, moss-like foliage, and aromatic odor.

No references cited.

ABRAHAM G. STONE, *Primary Examiner.*